(12) United States Patent
Lisitschew

(10) Patent No.: US 10,300,187 B2
(45) Date of Patent: May 28, 2019

(54) COUPLING FOR HOSE CONNECTIONS

(71) Applicant: B. BRAUN AVITUM AG, Melsungen (DE)

(72) Inventor: Swetlana Lisitschew, Munich (DE)

(73) Assignee: B. Braun Avitum AG, Melsungen (DE)

( * ) Notice: Subject to any disclaimer, the term of this patent is extended or adjusted under 35 U.S.C. 154(b) by 234 days.

(21) Appl. No.: 15/168,717

(22) Filed: May 31, 2016

(65) Prior Publication Data

US 2016/0361481 A1  Dec. 15, 2016

(30) Foreign Application Priority Data

Jun. 10, 2015  (DE) .................. 10 2015 109 158

(51) Int. Cl.
| | | |
|---|---|---|
| *A61M 1/16* | (2006.01) | |
| *A61M 39/12* | (2006.01) | |
| *F16L 33/00* | (2006.01) | |
| *B01D 61/28* | (2006.01) | |
| *B01D 61/30* | (2006.01) | |
| *A61M 1/14* | (2006.01) | |
| *A61M 39/10* | (2006.01) | |

(52) U.S. Cl.
CPC .......... *A61M 1/1621* (2014.02); *A61M 39/12* (2013.01); *B01D 61/28* (2013.01); *B01D 61/30* (2013.01); *F16L 33/00* (2013.01); *A61M 1/14* (2013.01); *A61M 2039/1088* (2013.01); *B01D 2313/13* (2013.01)

(58) Field of Classification Search
CPC .................. A61M 1/14; A61M 1/1621; A61M 2039/1088; A61M 39/12; B01D 2313/13; B01D 61/28; B01D 61/30; F16L 33/00; F16L 41/001; F16L 41/02; F16L 41/021; F16L 41/023; F16L 41/04
See application file for complete search history.

(56) References Cited

U.S. PATENT DOCUMENTS

| | | |
|---|---|---|
| 8,844,336 B2 | 9/2014 | Sagebiel |
| 2009/0293713 A1 | 12/2009 | Ibarra Romero |

(Continued)

FOREIGN PATENT DOCUMENTS

| | | |
|---|---|---|
| DE | 102005002552 | 7/2006 |
| DE | 20 2006 019 420 | 4/2007 |

(Continued)

OTHER PUBLICATIONS

European Search Report for European Application No. 16172381.2, dated Nov. 10, 2016, including English translation, 18 pages.

(Continued)

*Primary Examiner* — John Kim
(74) *Attorney, Agent, or Firm* — RatnerPrestia

(57) ABSTRACT

A hose mount of a blood treatment machine, having a hose connection element as a component of the machine's internal hosing including at least one rigid sleeve portion that is adapted to position a flexible hose radially outside over the free end of the at least one sleeve portion, an axial stop formed or arranged on the outer circumference of the sleeve portion at a distance from the free end, and a flexible collar arranged or formed on the at least one sleeve element toward the free end with an axial distance to the axial stop in order to define an external circumferential groove between itself and the axial stop.

12 Claims, 3 Drawing Sheets

(56) References Cited

U.S. PATENT DOCUMENTS

2013/0328304 A1 12/2013 Stenzel et al.
2015/0144717 A1 5/2015 Turk

FOREIGN PATENT DOCUMENTS

| DE | 202006005685 | 9/2007 |
| DE | 202009011641 | 4/2010 |
| DE | 20 2010 005 965 | 8/2011 |
| EP | 0821192 | 1/1998 |
| EP | 2 372 330 | 10/2011 |
| EP | 2 671 611 | 12/2013 |
| FR | 2939862 | 6/2010 |
| WO | 2004073764 | 9/2004 |
| WO | 2014201358 | 12/2014 |

OTHER PUBLICATIONS

European Search Report, with translation, for DE 10 2015 109 158.5 dated Jan. 13, 2016.

COUPLING FOR HOSE CONNECTIONS

CROSS REFERENCE TO RELATED APPLICATIONS

This application claims priority to German Application DE 10 2015 109 158.5 filed Jun. 10, 2015, the contents of such application being incorporated by reference herein.

FIELD OF THE INVENTION

The present invention relates to a coupling for hose connections, in the following simply referred to as a "hose connector", according to the preamble part of the independent claim.

BACKGROUND OF THE INVENTION

In particular with blood treatment machines such as dialysis machines, individual machine components such as heat exchangers, pumps, dialyzers, etc. are fluidically coupled to each other with flexibly bendable hoses. The use of such hoses allows to install the respective machine components individually or in a selected allocation in or on racks which can be pulled out partially from the machine housing for repair and/or maintenance purposes in order to improve their accessibility.

In order to avoid any entangling of the hoses and to reduce the risk of damaging individual hoses, one makes use of the measure of combining lines into so-called line harnesses which is known in particular from automotive engineering. Stated in other words, individually selected hoses are mechanically combined in the simplest case over a predetermined hose length with cable ties. This increases their overall resistance to kinking, so that the risk of damage can be reduced. At the same time, the hose confusion is reduced to a limited set of "hose harnesses" which can be arranged more clearly.

For supporting the hoses on/in the machine, mainly the machine components themselves are used, which are interconnected by hoses. Incidentally, the hoses are laid freely in space partially as a single hose or partially as hose bundles; here, neither hose guides nor hose fasteners are provided which contribute to the positioning and/or fixation of the hoses in the machine.

DESCRIPTION OF THE RELATED ART

The document EP 2 372 330 discloses an air bubble detector as an exemplary component of a blood treatment machine. Said detector comprises a mount which can be fastened to a machine housing and on which at least one ultrasonic sensor is arranged in order to detect air and/or gas bubbles in a flowing liquid. Integrated in the mount is a flow channel comprising connector pieces or muffs to which connection hoses can be attached. In this way, it is not only the detector which is retained on the housing, but also the connected hoses are held thereon.

Further, EP 2 671 611 shows a hose connection means (fluidic socket) which can be detachably mounted in an opening of a housing of a medical device and comprises a connection element to which a disposable article outside the housing can be selectively connected. This means that a fluidic connector (socket) for an external hose system is disclosed, which connector can be fixed or is fixed in a correspondingly dimensioned through-hole of a machine housing. The housing's external connection element of said known connector, for instance a Luer connector, is connected—via a hollow web as a middle portion of the hose connection means—to a connector muff for the housing's internal hose system, which connector muff can be introduced through the opening of the housing into the housing interior. Further, the hose connection means comprises a separates spring element which can be removably attached to the web in such a manner (comparable to an axial snap ring) that the hose connection means is supported on the housing with the spring element in an axially elastic fashion. In this respect, also this known hose connection means represents a further example of a machine component in the previously described sense, in the present case for the fluidic connection of external equipment.

It can be seen from the previous description of the prior art that the supporting and fixing of hoses within a blood treatment machine is achieved only by available machine components; what is more, the hoses are loosely supported. In the case of a maintenance or repair, if individual drawers/racks which have machine components supported thereon are partially pulled out of the machine housing and pushed back again, the hoses arranged thereon may get kinked, clamped or even torn off. This form of damage cannot necessarily be eliminated even by combining the hoses to hose harnesses or bundles.

Of course, there is the theoretical possibility to place the machine components (which are interconnected by hoses) in the machine housing in such a manner that the hoses are stably kept in their spatial position as best as possible. In practice, however, this measure has its limitations, as the individual machine components have different functions and hence have sizes which are to be taken into consideration when arranging them in the machine housing. Moreover, some components have to be arranged at different predetermined places in the machine housing depending on their function, and hence their arrangement cannot be varied or only to a very limited extent.

SUMMARY OF THE INVENTION

In view of these problems, it is an object of the present invention to provide a hose support possibility for hoses of a blood treatment machine which is as simple as possible, can be applied as easily as possible and without any larger effort and which is able—in addition to the normally available machine components of the blood treatment machine according to the above definition—to hold the individual hoses more stably in their spatial position.

This object is achieved by a hose mount of a blood treatment machine comprising the features of the independent claim.

A basic idea of the present invention is to alter suitable elements of the hosing (other than the machine components according to the above definition) such that they have the additional function of hose mounts. These suitable elements should preferably be a constituent part of the hosing and have a sufficiently high stiffness and stability in order to be able to transfer holding forces to a machine housing and in this way to fix the hoses in their position in space without any damage.

Here, it is referred to the fact that simple cable ties—which can be laid in a known manner around a flexible line as around cables—are not very suitable for flexible fluid hoses, as they would carve into the hoses in line-shaped manner and hence could form predetermined kinking points. So-called pipe clamps show a similar behavior—they indeed offer a more extensive support, but still have the problem of compressing the flexible hose and thus are suitable for rigid pipelines only.

So-called hose connectors and/or junctions have turned out to be especially suitable elements of this kind. These are comparably rigid hosing elements preferably made of plastics or metal, with which two hoses are fluidically and firmly coupled to each other and/or a hose is branched off in two or more further hoses.

In the simplest case, such a hose connection element is a rigid sleeve which has a predetermined length and whose both sides are adapted to put a hose radially outside over them. It is also possible that the hose connection element with the same functional principle is a T-, Y or X-piece which in this case additionally serves as a flow junction of the hosing. Such hose connection elements are constituents of the hosing itself and are not provided for being selectively coupled or uncoupled in regular operation of the blood treatment machine. Rather, these are elements which serve for providing the hosing (of the fluid flow system) and hence are intended/provided as being "not selectively detachable".

According to aspects of the invention, provision is made to additionally (integrally) form or provide such a (fixed) hose connection element for the (firm, i.e. not adapted for selectively uncoupling and coupling) connection of hoses to at least one flow channel or sleeve element/portion with a flexible collar which is axially spaced from a radially outer, preferably rigid stop protrusion on the flow channel or the at least one sleeve element/portion in order to define an axial gap (or external circumferential groove) between itself and the axial stop.

Such a hose connection element is able to cooperate at almost any place in the machine housing with a housing wall or a holding bracket that can be fixed to the machine housing, by the housing wall or the holding bracket comprising a through-hole whose diameter substantially corresponds to the diameter of the at least one sleeve element/portion (or is smaller than the external diameter of the flexible collar) into which the hose connection element can be inserted with its at least one sleeve portion, accompanied by a flexible and temporary deformation of the collar.

This results in the wall or the holding bracket being axially retained in the circumferential groove between the collar and the stop, so that a hose can be attached at both sides of the at least one sleeve element/portion.

According to aspects of the invention, the mounting is the hosing-integrated hose connection element (and not a machine component) which for the purpose of force introduction cooperates with the housing wall and/or a holding bracket mounted on the housing without the add-on of a holding arm integrally arranged thereon or such similar holding device. The flexible collar allows a one-side, simple assembly without additional locking means.

It is preferred that the collar has a dowel shape such that the at least one sleeve element/portion of the hose connection element equipped therewith can be simply plugged from one side into the receiving hole of the housing wall or of the holding bracket mounted thereto, and the collar automatically and in resilient fashion spreads on the other side and in this way axially holds the wall or bracket between itself and the sleeve-side stop.

Further, the hose connection element may preferably be a simple hose sleeve having two sleeve ends to which a hose is attached, or it is a flow junction e.g. in the form of a Y-, T- or X-type branching piece or the like in which one of the several sleeve portions is provided or formed with the previously described collar and preferably with the additional axial stop for attaching hose ends.

The invention allows to achieve the following advantages:

- The hoses are laid at a defined position in the space of the blood treatment machine. This avoids situations where hoses are damaged, bent or squeezed.
- In blood treatment machines (dialysis machines) with slide-in technology, the hoses can be directly guided through the slide-in plates which in that case represent movable housing walls. This means that there is no need to make any detours "outside" the slide-in plate. In this context, they are fixed in the machine space in a defined manner and at the same time they are strain-relieved. Moreover, the hose lengths and thus the hose volumes can be reduced. This has a positive impact on e.g. the consumption of the dialysis liquid, the power consumption, the consumption of disinfectants, the time needed for disinfection, etc.
- The hoses can be put through fixed housing walls. In doing so, they are fixed in a defined manner, are strain-relieved and at the same time sealed in the housing's feed-through. This allows to prevent the hoses from accidentally tearing off at points where they are connected to machine components.
- A one-sided (one-hand) assembly of the hose connection element is made possible by simply putting or inserting the at least one sleeve portion into the through-hole in the machine wall or holding bracket. An additional axial fixation is not required.
- The functions "coupling," "feed-through," "strain relief," "hose connection" and "hose fixation" are combined in one part.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

As can be basically taken from the Figures, the hose connection element 1 according to aspects of the invention has the same construction principle as known hose connectors, so that reference can be made to the general prior art at this point. By way of example, the hose connection element of the invention (hose connector) 1 according to FIGS. 4a to 4e may have the form of a sleeve-like double muff, Y junction, T junction, elbow piece or X junction (cross junction), with the individual sleeve portions which preferably are made of plastics or metal being integrated to a single rigid component by injection-molding or screwing or putting them together, for example. All these shapes (which are known per se) are also conceivable as a reducing hose connector, e.g. if a small diameter hose is to be changed to a large diameter hose or vice versa. These geometries basically fulfil the function of a hosing-integrated hose connection (which is not provided for being selectively detached in regular operation).

Figure 1:
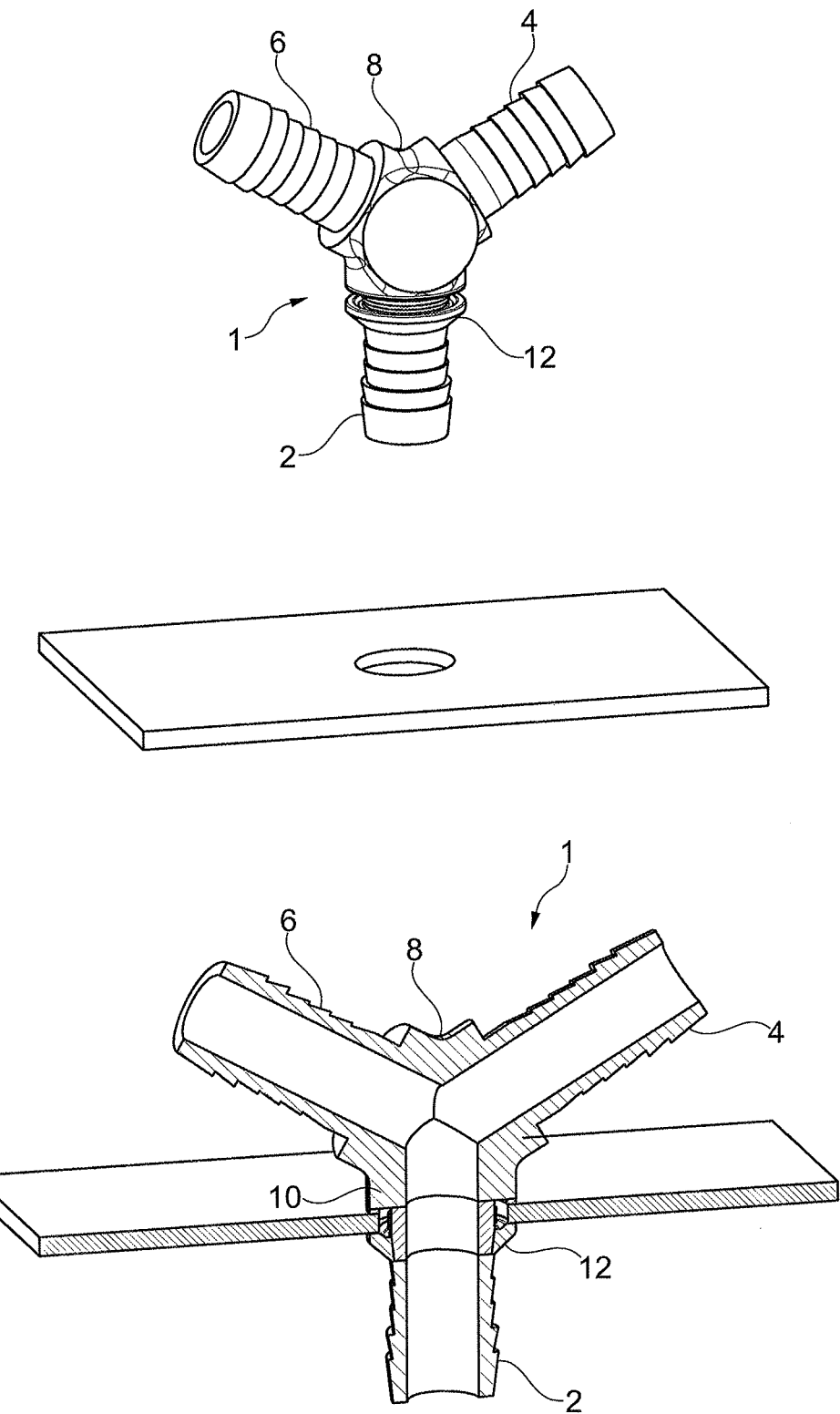
FIG. 1 shows the functional principle of a hose connection element according to aspects of the invention on the basis of an exemplary Y junction.
Figure 2:
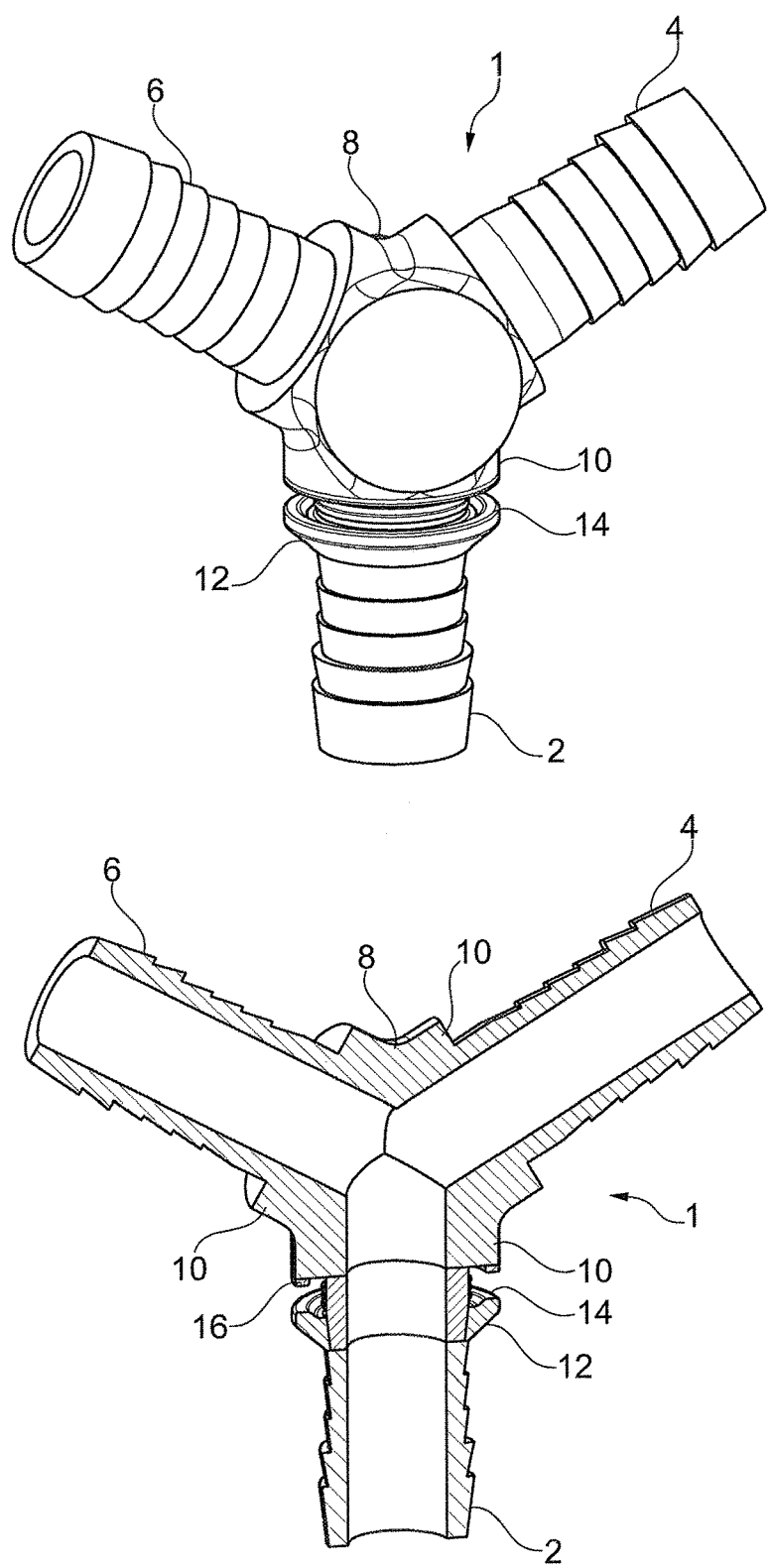
FIG. 2 shows a side view and an associated sectional view of the hose connection element according to aspects of the invention on the basis of the exemplary Y junction in an enlarged view.
Figure 3:
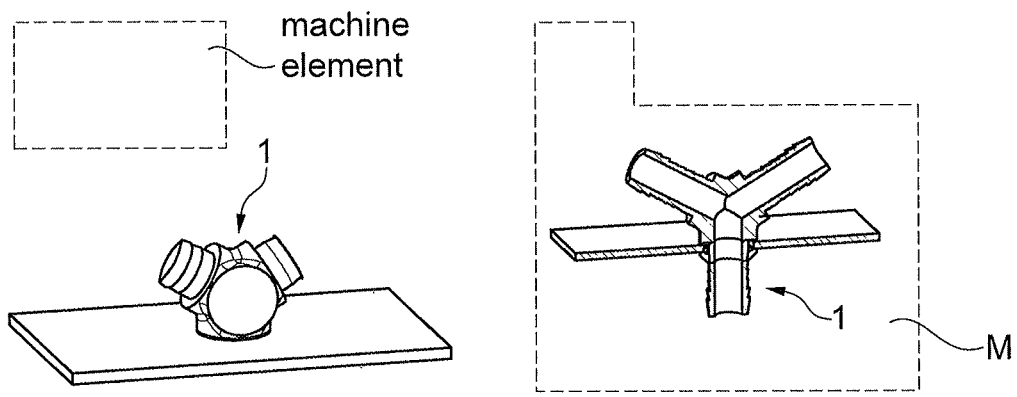
FIG. 3 shows a side view and an associated sectional view of the hose connection element according to aspects of the invention on the basis of the exemplary Y junction in the installed state.
Figure 4A:
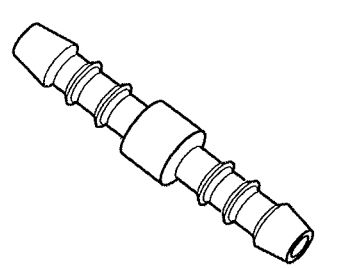
FIGS. 4a to 4e show variants of a hose connection element according to aspects of the present invention.
Figure 4B:
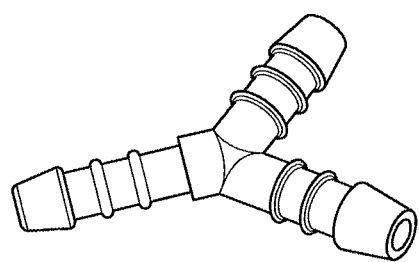
Figure 4C:
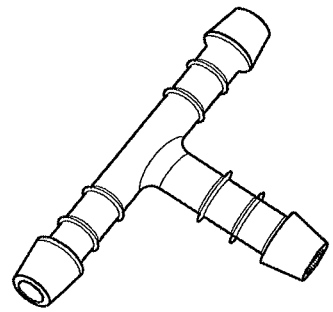
Figure 4D:
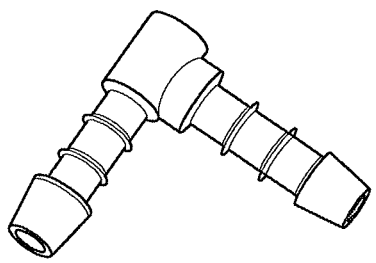
Figure 4E:
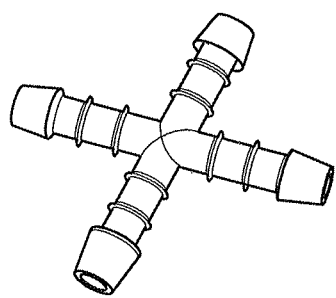

FIGS. 1 to 3 show an example of the modification, according to aspects of the invention, of the previously described basic designs on the basis of a Y junction; at this point, it is explicitly referred to the fact that the modification described below may be provided for all illustrated designs (and also for any other designs known beyond) for hose connectors of the present type.

According to FIG. 2, the Y junction which is exemplarily shown as the hose connection element/hose connector 1 according to aspects of the invention comprises three sleeve portions 2, 4, 6 in total intended for attaching hose ends which are to be connected to each other (see in particular FIG. 3) and converging in joint-like fashion in a central junction node 8 such that the sleeve portions 2, 4, 6 are fluidically coupled to each other. The central junction node 8 represents an agglomeration of material, whereby an external axial stop 10 is formed on at least one sleeve portion 2 (preferably on all sleeve portions 2 to 6), said axial stop normally functioning as an axial attachment stop for the hose end attached in each case. As the central junction node 8 and preferably also the sleeve portions 2 to 6 are made of a rigid material such as plastics (thermoplastic material) or metal, the at least one axial stop 10 is also rigid and substantially dimensionally stable.

In addition to the axial stop 10, the at least one sleeve portion 2 comprises a collar or bushing 12 which is axially spaced from the axial stop 10 and is made of a material which is flexible (elastic) as compared to the axial stop 10 such as an elastomer material, forming a radially outer circumferential groove between the axial stop 10 and the collar 12.

It can be seen on the basis of FIG. 2 that the longitudinal section of the collar 12 has the shape of a cone or dowel such that it radially tapers (in cup-like fashion) from its end facing the axial stop 10 toward the outer/free end of the sleeve portion 2. What is more, the collar 12 forms—at its front end facing the axial stop 10—an axially protruding and closed circumferential sealing lip 14 which is opposite to a closed circumferential sealing lip 16 correspondingly formed/arranged on the front end of the axial stop 10.

The collar 12 may be affixed to the one sleeve portion 2 by gluing, by putting it on the sleeve portion or by forming it in one piece with it. In any case, once the collar has been formed/mounted, it preferably forms a unit with the one sleeve portion 2 and hence a constituent part of the hose connection element 1 according to aspects of the invention.

The circumferential groove has a groove width which allows to receive the housing wall or a wall-mounted holding bracket of a blood treatment machine or dialysis machine M which is illustrated in FIG. 3 only as a system limitation.

Stated in other words, the collar 12 is placed on the at least one sleeve portion 2 in such a manner that the axial distance defined between the collar and the axial stop 10 substantially corresponds to the width of a housing wall or a wall-mounted holding bracket of the blood treatment machine. Such a housing wall or holding bracket is symbolically represented by a plate in FIGS. 1 and 3. Accordingly, the housing wall or holding bracket has a through-hole with a hole diameter substantially corresponding to the external diameter of the groove bottom, with the external diameter of the groove bottom preferably being larger than the (average) external diameter of the at least one sleeve portion 2, as can be taken in particular from FIG. 2. Here, the groove bottom may be formed either by the at least one sleeve portion 2 made of a rigid material or by the collar 12 made of a flexible material, with the latter solution having the advantage of compensating tolerances of the hole diameter.

By means of the collar/bushing 12, the hose connector 1 according to aspects of the invention can be axially inserted from one side through the through-hole/recess in the housing wall or holding bracket. In doing so, the geometry of the flexible collar 12 engages behind the wall or holding bracket, whereby it is retained in the axial groove between the collar 12 and the axial stop 10. At the same time, the two sealing lips 14, 16 facing each other are pressed against the wall or holding bracket, whereby the hose connector 1 is sealed off with respect to the wall/the holding bracket. In the next step, the hoses can be put onto all the sleeve portions 2 to 6 as shown in FIG. 3.

The flexibility of the collar 12 allows to easily compensate any tolerances of the wall thickness, and the collar 12 is able to accommodate different wall thicknesses. In addition, the flexible collar 12 is capable of absorbing vibrations and attenuating noise. Finally, the elasticity of the collar 12 allows to accommodate any movements due to temperature changes or external concussions without loosing the tightness between itself and the wall/the holding bracket.

Finally, it is referred to the fact that the recess in the wall (through which the collar is to be inserted) or in the holding bracket (to which the collar is to be fastened) may be implemented so as to be rotationally symmetrical or rotationally asymmetrical or simply as a U-shaped recess.

The invention claimed is:

1. A hose connection element for a blood treatment machine internal hosing comprising:
   at least one rigid sleeve portion, each rigid sleeve portion having a free end, wherein the at least one rigid sleeve portion is adapted to be inserted into a through-hole of a housing wall of the blood treatment machine or into a through-hole of a holding bracket fixed to the housing wall of the blood treatment machine;
   a rigid axial stop formed or arranged on an outer circumference of one or more of the at least one rigid sleeve portion a distance from the free end thereof; and
   a flexible collar formed or arranged on the one or more of the at least one rigid sleeve portion between the rigid axial stop and the free end and spaced from the rigid axial stop an axial distance to define an external circumferential groove between the flexible collar and the rigid axial stop, wherein when the at least one rigid sleeve portion is inserted into the through-hole of the housing wall or the through-hole of the holding bracket, the flexible collar automatically and resiliently spreads on a side of the housing wall or holding bracket opposite the side of insertion, such that the housing wall or holding bracket is axially held between the flexible collar and the rigid axial stop in the external circumferential groove;
   wherein, when the housing wall or holding bracket is axially held between the flexible collar and the rigid axial stop in the external circumferential groove, an open end of a flexible hose is positioned radially around the free end of the at least one rigid sleeve portion such that the open end of the flexible hose is held by the free end of the at least one rigid sleeve portion.

2. The hose connection element according to claim 1, wherein the flexible collar has a dowel or funnel shape that tapers toward the free end of the one or more of the at least one rigid sleeve portion.

3. The hose connection element according to claim 1, wherein the flexible collar forms or has a circumferentially closed sealing lip on a front end of the flexible collar facing the rigid axial stop, the sealing lip of the flexible collar protruding axially toward the rigid axial stop.

4. The hose connection element according to claim 3, wherein the rigid axial stop forms or has a circumferentially closed sealing lip on a front end of the rigid axial stop facing the flexible collar, the sealing lip of the rigid axial stop protruding axially toward the collar.

5. The hose connection element according to claim 1, wherein the flexible collar is made from an elastomer material applied on the one or more of the at least one rigid sleeve portion by injection-molding, gluing or stretching.

6. The hose connection element according to claim 1, wherein a bottom of the external circumferential groove is formed by the flexible collar.

7. The hose connection element according to claim 1, wherein the hose connection element includes at least two rigid sleeve portions forming a straight double muff, an elbow piece or a Y-, T- or X-piece.

8. The hose connection element according to claim 7, wherein only one of the at least two rigid sleeve portions is provided with the flexible collar.

9. A blood treatment machine comprising:
a housing for the fluidic interconnection of a plurality of machine elements that are fixed to at least one of the housing or racks supported in the housing, wherein the housing includes a housing wall and at least one through-hole of the housing wall or a through-hole of a holding bracket fixed to the housing wall; and
at least one hose connection element according to claim 1, wherein:
the at least one rigid sleeve portion is adapted to be inserted into at least one of the through-hale of the housing wall or the through-hole of the holding bracket fixed to the housing wall;
when the at least one rigid sleeve portion is inserted into at least one of the through-hole of the housing wall or the through-hole of the holding bracket, the flexible collar automatically and resiliently spreads on a side of the housing wall or holding bracket opposite the side of insertion, such that the housing wall or holding bracket is axially held between the flexible collar and the rigid axial stop in the external circumferential groove; and
when the housing wall or holding bracket is axially held between the flexible collar and the rigid axial stop in the external, circumferential groove, an open end of a flexible hose is positioned radially around the free end of the at least one rigid sleeve portion such that the open end of the flexible hose is held by the free end of the at least one rigid sleeve portion.

10. The blood treatment machine according to claim 9, wherein the blood treatment machine is a dialysis machine.

11. The blood treatment machine according to claim 9, wherein a recess in the form of at least one of a rotationally symmetrical, rotationally asymmetrical, or U-shaped opening is formed in at least one wall of the housing, a rack within the housing, or a holding bracket mounted to the at least one wall, the diameter of the opening corresponding to a bottom of the external circumferential groove between the flexible collar and the rigid axial stop of the one or more of the at least one rigid sleeve portion of the hose connection element.

12. The blood treatment machine according to claim 9, wherein the thickness of at least one of the at least one wall of the housing, the rack or the holding bracket mounted to the at least one wall of the housing corresponds to a width of the groove between the flexible collar and the rigid axial stop of the one or more of the at least one rigid sleeve portion of the hose connection element.

* * * * *